United States Patent
Slocum, Jr. et al.

(10) Patent No.: US 7,863,897 B2
(45) Date of Patent: Jan. 4, 2011

(54) METHOD AND APPARATUS FOR CHARACTERIZING THE TEMPORAL RESOLUTION OF AN IMAGING DEVICE

(75) Inventors: Alexander H. Slocum, Jr., Bow, NH (US); Rajiv Gupta, Wayland, MA (US); Stephen E. Jones, Cleveland Heights, OH (US); Alexander H. Slocum, Sr., Bow, NH (US)

(73) Assignee: The General Hospital Corporation, Boston, MA (US)

( * ) Notice: Subject to any disclaimer, the term of this patent is extended or adjusted under 35 U.S.C. 154(b) by 114 days.

(21) Appl. No.: 12/206,279

(22) Filed: Sep. 8, 2008

(65) Prior Publication Data

US 2009/0315557 A1 Dec. 24, 2009

Related U.S. Application Data

(60) Provisional application No. 60/967,833, filed on Sep. 7, 2007.

(51) Int. Cl.
*G01V 3/00* (2006.01)

(52) U.S. Cl. .................................... 324/309; 324/307

(58) Field of Classification Search ......... 324/300–322; 600/407–445; 378/4, 5, 8, 9, 16, 18, 37, 378/62
See application file for complete search history.

(56) References Cited

U.S. PATENT DOCUMENTS

| | | | |
|---|---|---|---|
| 2,356,736 A * | 8/1944 | Blaes .................... | 280/11.209 |
| 5,056,130 A | 10/1991 | Engel | |
| 5,954,647 A * | 9/1999 | Bova et al. .................. | 600/407 |
| 6,561,695 B2 | 5/2003 | Proksa | |
| 6,683,934 B1 * | 1/2004 | Zhao et al. ..................... | 378/9 |
| 6,715,918 B2 | 4/2004 | Mitschke et al. | |
| 6,778,689 B1 * | 8/2004 | Aksit et al. ................. | 382/128 |
| 6,978,936 B2 * | 12/2005 | Tsikos et al. ........... | 235/462.01 |
| 7,012,986 B1 | 3/2006 | Chao et al. | |
| 7,016,456 B2 | 3/2006 | Basu et al. | |
| 7,174,200 B2 * | 2/2007 | Salerno et al. .............. | 600/420 |
| 7,352,840 B1 * | 4/2008 | Nagarkar et al. ............. | 378/19 |
| 7,444,011 B2 * | 10/2008 | Pan et al. ..................... | 382/131 |
| 7,684,846 B2 * | 3/2010 | Johnson et al. ............. | 600/407 |
| 2004/0044279 A1 * | 3/2004 | Lewin et al. ................. | 600/407 |
| 2004/0092813 A1 * | 5/2004 | Takizawa et al. ............ | 600/423 |
| 2004/0227069 A1 | 11/2004 | Sendai et al. | |
| 2005/0054913 A1 * | 3/2005 | Duerk et al. ................. | 600/423 |
| 2008/0114235 A1 * | 5/2008 | Unal et al. ................... | 600/411 |
| 2009/0091322 A1 * | 4/2009 | Posse ......................... | 324/307 |
| 2009/0092284 A1 * | 4/2009 | Breed et al. ................. | 382/103 |
| 2009/0234243 A1 * | 9/2009 | Schneider et al. ........... | 600/544 |

\* cited by examiner

*Primary Examiner*—Brij B Shrivastav
(74) *Attorney, Agent, or Firm*—Quarles & Brady LLP (57) ABSTRACT

A system and method for determining the temporal resolution of a tomographic imaging device uses an apparatus to drive one or more dynamic phantoms composed of multiple materials. The apparatus is placed at or near the isocenter of the imaging device and the one or more phantoms are moved to produce a plurality of dynamic features, each having a specified frequency. The dynamic features are imaged with the device and the acquired image data corresponding to the dynamic features is analyzed to determine a temporal modulation transfer value at each of the known specified frequencies. The temporal resolution of the imaging device is determined using these temporal modulation transfer values.

25 Claims, 10 Drawing Sheets

METHOD AND APPARATUS FOR CHARACTERIZING THE TEMPORAL RESOLUTION OF AN IMAGING DEVICE

CROSS-REFERENCE TO RELATED APPLICATIONS

This application claims the benefit of U.S. Provisional Patent Application Ser. No. 60/967,833 filed on Sep. 7, 2007 and entitled "METHOD AND APPARATUS FOR CHARACTERIZING THE TEMPORAL RESOLUTION OF AN IMAGING DEVICE".

STATEMENT REGARDING FEDERALLY SPONSORED RESEARCH

Not applicable.

FIELD OF THE INVENTION

The invention relates to a system and method for determining temporal modulation transfer function (t-MTF) values, at multiple frequencies of a tomographic medical imaging device. These values are then used to derive the temporal resolution of the imaging device.

BACKGROUND OF THE INVENTION

Tomographic medical imaging devices or scanners such as computed tomography (CT) and magnetic resonance (MR) imaging devices are increasingly used for visualizing dynamic processes. In particular, the recent advent of Volumetric Computed Tomography (VCT) could have as strong an impact on medical imaging as that which resulted from the development of standard CT in the 1970's. Specifically, VCT relies on X-rays being directed through an object to be imaged, and large planar detectors for acquiring image data at a plurality of views. VCT utilizes mathematical algorithms to process the acquired image data to create 3-D images of the human body and its systems. These images have the potential to aid in the detection and diagnosis of disease. Accordingly, VCT also has the potential to be used in the development of new treatments and procedures. VCT is also capable of dynamic imaging, such as capturing a 3-D video of a beating heart or the perfusion of organs. Similar methods have been developed for volumetric MR, Ultrasound, and other tomographic imaging modalities.

However, before a tomographic imaging device can be accurately and safely used in the treatment of patients, it is important to define its boundaries and limitations. The temporal resolution of an imaging device indicates the fastest movements that the imaging device can resolve and faithfully reproduce. For example, if the heart of a small animal is beating extremely fast, such as 200 or 300 beats per minute, then an image of the heart produced by a typical imaging device will be blurred if the temporal resolution of the device cannot sufficiently capture this motion. Thus, the higher the temporal resolution of an imaging device, the more capable it is of producing quality images of fast moving structures inside its imaging volume. However, while methods exist for defining and measuring spatial resolution in terms of a modulation transfer function, there is no standard method for measuring temporal resolution. Prior art methods for measuring the temporal resolution of a tomographic imaging device are limited to using indirect metrics such as rotation time or the image acquisition time. In addition, a single numerical value has been used to describe the temporal resolution. Because the temporal response of an imaging device declines as faster and faster changes in the object space are imaged, the concept of progressive degradation of performance has not previously been formalized.

Therefore, it would be desirable to have a system and method for accurately determining the temporal resolution of an imaging device.

SUMMARY OF THE INVENTION

The present invention overcomes the aforementioned limitations by providing a system and method for acquiring data that can be used to generate a t-MTF for a given imaging device. For a time-varying signal at a specified frequency, a value of temporal modulation transfer describes how well signal amplitude modulation in the object space is represented in the image space. There is a direct correlation between image modulation and the signal frequency, similar to the dependence of optical image quality on spatial frequency seen in optical systems.

An apparatus (or "phantom") which fits in the imaging volume of a medical imaging device can be used to determine the temporal modulation transfer function of the imaging device at a set of specified frequencies. The apparatus is operable to generate a plurality of time-varying volumes termed dynamic features. These dynamic features can be imaged, with each having a corresponding specified frequency within a set of specified frequencies. One embodiment of the apparatus includes one or more rotating slotted disks which are each mounted to the respective rotating ring gears of planetary gear assemblies. For most applications, two rotating ring gears and corresponding attached slotted disks should be sufficient but very high resolution and broader dynamic range can be obtained by using more. Each planetary gear assembly includes a sun gear, all of which are driven by a common drive shaft at a constant speed. Each planetary gear assembly also includes a planet gear that is driven by the sun gear and supported on a fixed shaft. Each planet gear drives a corresponding ring gear, and in turn, one of the slotted disks at a specified speed. Each slotted disk has a plurality of rings at different radii, wherein each ring is made up of one or more equally spaced slots or cuts. When the drive shaft is driven at a specified speed by a motor, the equally spaced slots generate dynamic features in an imaging plane. For example, in an imaging plane transverse to the disk, the rotation of the disks produces mostly static images with small sub-regions having corresponding square wave signals each of a known specified frequency. Through this arrangement, up to two decades or more of scan-able input frequencies can be generated simultaneously using a single constant speed motor and drive shaft.

A series of images of the rotating disks can be obtained using the imaging device which can be analyzed to locate the dynamic features. The temporal characteristics of these features are then analyzed and a temporal modulation transfer value is calculated at each frequency. One can then plot the temporal modulation transfer values against their respective frequency. The resulting graph should show a monotonic decline in the temporal modulation transfer function values as frequency is increased. For example, characterization of one imaging device resulted in a measured 85% temporal modulation transfer function values at low frequency which deteriorated to approximately 2% at high frequency. Analogous to spatial resolution, one can then define the temporal resolution of the scanner to be the frequency for which there is a specified amount of modulation transfer, such as 10%.

Such an apparatus is efficient, compact, easily adjustable, and easy to operate. Furthermore, the apparatus utilizes available machine elements that are designed to fit into a relatively small space. However, even though many of the elements are custom engineered and designed, their actual form is not difficult to manufacture, and some, such as all-plastic ball bearings, are commercially available. The result is an all-plastic machine that is compatible with multiple imaging modalities, such as CT and MR imaging devices.

The apparatus can be adapted to different imaging modalities depending on the property being measured. For example, for ultrasound imaging the apparatus can be immersed in a fluid so that dynamic behavior of the slotted rings and the square wave they generate can be imaged. Similarly, the slots in the rings can be loaded with appropriate MR sensitive materials so that T1, T2, or other MR properties can be imaged. The t-MTF of any MR pulse sequence can then be measured using a similar t-MTF phantom.

DETAILED DESCRIPTION OF THE INVENTION

The present invention includes a system and method for characterizing the temporal resolution of an imaging device. As will be described, the present invention includes a method for developing and using a temporal modulation transfer function (t-MTF). Specifically, the present invention includes a system having a series of gear assemblies to simulate a wide range of rotational velocities in an area or volume to be imaged. The present invention further includes a system including one or more slotted disks. Each disk allows for the simultaneous acquisition of different dynamic processes, each having a different temporal frequency. Image data corresponding to these processes, and their associated frequencies, is analyzed using t-MTF to generate a graph of signal modulation versus frequency.

Figure 1:
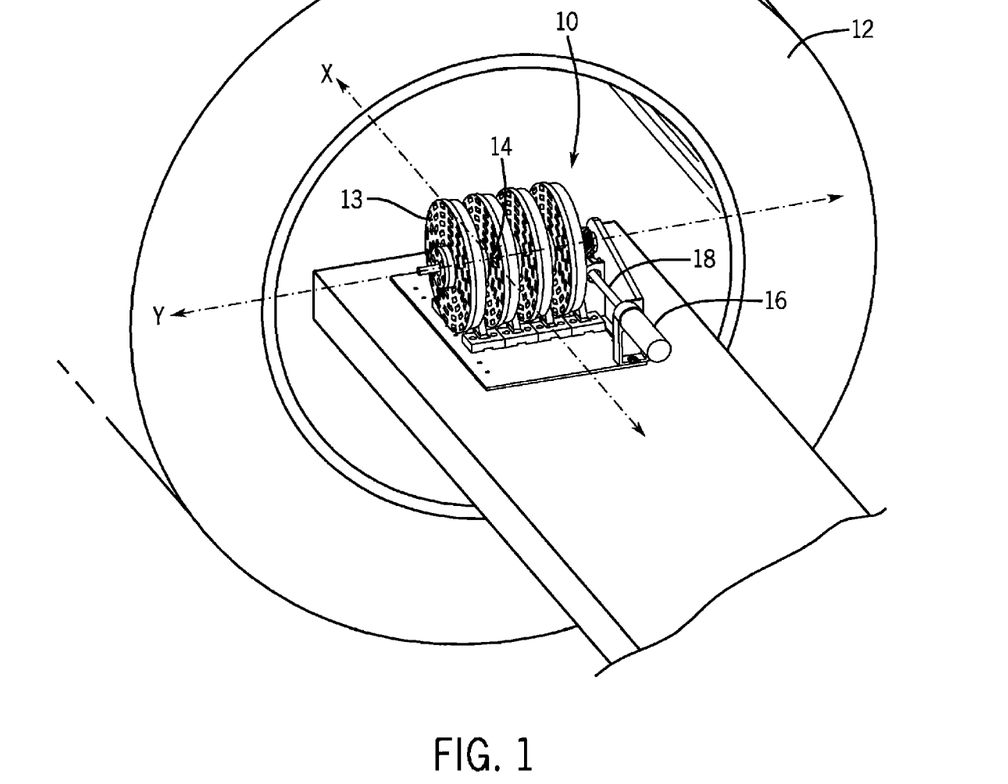
FIG. 1 is an illustration of the bore of a CT imaging device showing one embodiment of an apparatus for characterizing temporal resolution at the isocenter or "sweet spot" of the CT imaging device and showing an X-Y coordinate system.

Referring now to FIG. 1, a system for characterizing temporal resolution 10 is designed to be positioned inside a scanning area or volume of an imaging system 12. In the illustrated example this happens to be the bore of a CT machine. However, it is contemplated that the present invention may be utilized with other imaging modalities, such as MRI machines or any tomographic imaging device. As will be described, the system 10 includes a set of disks—four disks in the example shown in FIG. 1—that acts as "dynamic phantom" 13. These disks are arranged at the isocenter 14 or "sweet spot" of the imaging device 12.

The isocenter 14 is located at the intersection of the X and Y axes of the imaging system 12. The sensitivity of a medical imaging device, in terms of image quality, varies with respect to the object's position inside the scanning volume. Proximity to the axis of rotation of the gantry (X axis) and the mid-plane of the scanning bore (Y axis) are major factors in determining resolution and image quality. Because the isocenter of the imaging device is the most sensitive part of the machine and provides the best image quality and highest scanning resolution, it follows that the preferred placement for the dynamic phantom 13 when performing a process to characterize the temporal resolution of the imaging system is at or near the isocenter of the imaging device. In addition, the dynamic phantom is oriented such that the plane in which the disks rotate is perpendicular to the tomographic imaging plane of the scanner. This ensures that the rotational motion does not generate artifacts in the imaging plane.

In the field of medical imaging, a phantom refers to an object that is used in some cases to represent anatomical features of biological organisms, and in others to allow operators to calibrate different characteristics of the imaging device. However, traditional phantoms are static in nature. That is, they have a fixed composition and are not suitable for characterizing time varying processes.

On the other hand, the system 10 includes a motor 16 connected via a drive shaft 18 to drive the dynamic phantom 13 during operation. It is contemplated that the motor 16 may be a DC motor controlled by an open-loop drive. However, because of the importance of maintaining a substantially constant rotational velocity, it is preferable for the motor 16 to be a motor with encoder feedback or it can be velocity controlled using a closed-loop controller. The specific size of the motor is determined based on an estimate of initial static torque, along with an estimated maximum motor output required to rotate one or more planetary gear assemblies.

The material used for the disks 13, the shaft 18, and all other components used in the dynamic phantom 13, including the motor 16, should be compatible with the imaging device being used. For example, for MRI scanners, no ferromagnetic material may be used. For this application piezoelectric motor may be used to drive the assembly of disks. In addition, the material for the disk and the slots on them should be visible on the imaging device being characterized.

By driving the dynamic phantom 13, the system 10 is designed to generate "dynamic features" using a sequence of planetary gear assemblies whose sun gears are all driven from a common shaft driven by the one motor that is placed outside of the scanning area. As will be described, the dynamic phantom 13 includes one or more planetary gear assemblies that are driven by the drive shaft 18. By imaging during operation of the dynamic phantom 13, data is obtained that includes the time varying signals generated by the slotted disks, with each signal having a predetermined frequency.

Figure 2:
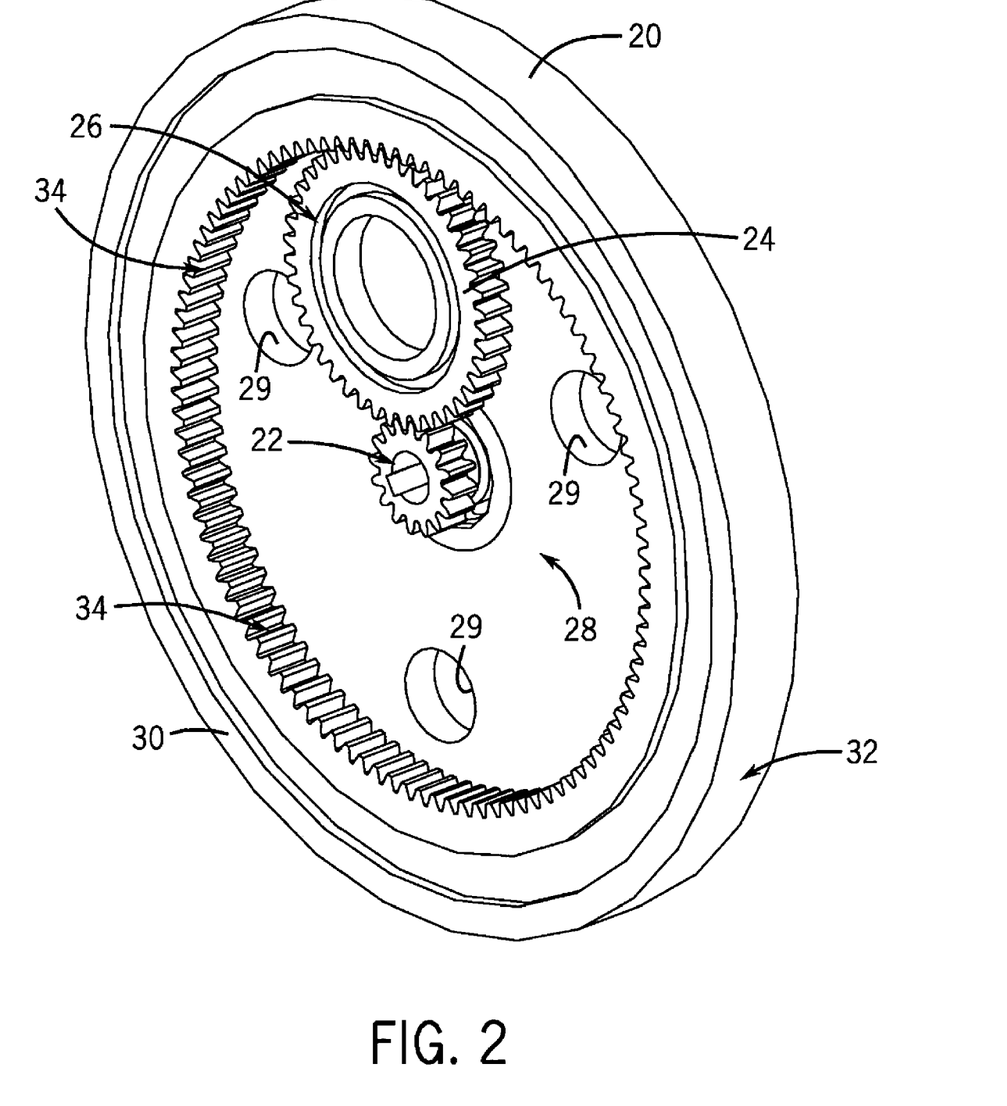
FIG. 2 is a perspective view of a single planetary gear assembly, representing a previous iteration of the present invention.

Referring now to FIG. 2, one configuration for a dynamic phantom having multiple, distinct contrast areas formed therein includes a single stage planetary gear assembly 20.

The gear assembly 20 includes a sun gear 22, which is mounted on the drive shaft 18 of FIG. 1, and driven by the motor 16. A planet gear 24 is arranged proximate to, but not fixed to, a plate 28 having formed therein a plurality of holes 29. The gear assembly 20 also includes an outer disk 30, which has an outer rolling element raceway of a bearing machined into its inner surface. The inner raceway of the bearing is machined into the outer surface of the plate 28 with the plurality of holes 29 on it. In addition, an internal ring gear 34, also machined into the inner surface of the outer disk 30, is then driven by the planet gear 24. Accordingly, during operation, the sun gear 22 is driven by the drive shaft, which in turn drives the planet gear 26. The planet gear 26 drives the internal ring gear 34. The plate 28 provides support to the disk 30, in which the internal gear 34 is machined, allowing the disk 30 to rotate. In accordance with the illustrated embodiment, another component may be mounted to the disk 30. As will be described, the plate 28 provides support, and the bearings allow the outer disk to rotate relative to it. As mentioned above and described below with respect to FIGS. 5 and 6, the plate 28 and associated driving components provide a surface on which a contrast area or volume can be mounted. To this end, the embodiment illustrated in FIG. 2 is designed specifically to operate as a dynamic phantom having multiple, distinct contrast areas (e.g., the solid materials, such as the plate 28, provide one distinct contrast in a reconstructed CT image and the holes 29 provide another distinct contract in the reconstructed CT image) for determining the t-MTF of a CT imaging system. However, as will be appreciated by those of skill in the art, the specific compositions used to create the multiple, distinct contrast areas may vary significantly, particularly, with imaging modality. The contrast areas are therefore modality specific. For CT, the different contrast areas have different density, and consequently, they appear different in the acquired images. For ultrasound, MRI or other tomographic modalities, the alternating contrast areas must be composed of appropriate material that simulates variations in the property being measured by the imaging modality.

To reduce cost and part count, all internal ring gears of each of the planetary gear assemblies are preferably the same size. During the design process, this can be achieved by setting the pitch diameter of the internal gear to a constant value, const, and determining appropriate diameters for the sun gears and planet gears according to:

$$const = \frac{D_{pitch\text{-}internal}}{2} = D_{pitch\text{-}planet} + \frac{D_{pitch\text{-}sun}}{2}.  \quad \text{Eqn. 1}$$

A 10% reduction in speed from each successive gear assembly to the next was initially outlined as the ideal configuration, although the Tables below illustrate that this is not feasible. Specifically, Table 1 shows example drive motor and gear parameters, while Table 2 shows an example analysis spreadsheet. It can be seen from Table 2 that utilizing an integer number of gear teeth will not result in a constant percentile reduction in speed.

TABLE 1

Motor and Gear Parameters

| Shaft Speed | 100 | Rpm |
| Internal Gear Diameter | 100 | Mm |
| Module | 1 | Mm/tooth |

TABLE 2

Analysis Spreadsheet

| Sun Gear | | | | Planet Gear | |
|---|---|---|---|---|---|
| Diameter (mm) | Number of Teeth | Gear Ratio | Speed Ratio | Diameter (mm) | Number of Teeth |
| 14.0 | 14.0 | 0.14 |  | 43.0 | 43.0 |
| 16.0 | 16.0 | 0.16 | 14.29% | 42.0 | 42.0 |
| 18.0 | 18.0 | 0.18 | 12.50% | 41.0 | 41.0 |
| 20.0 | 20.0 | 0.2 | 11.11% | 40.0 | 40.0 |
| 22.0 | 22.0 | 0.22 | 10.00% | 39.0 | 39.0 |
| 24.0 | 24.0 | 0.24 | 9.09% | 38.0 | 38.0 |
| 26.0 | 26.0 | 0.26 | 8.33% | 37.0 | 37.0 |
| 28.0 | 28.0 | 0.28 | 7.69% | 36.0 | 36.0 |
| 30.0 | 30.0 | 0.3 | 7.14% | 35.0 | 35.0 |
| 32.0 | 32.0 | 0.32 | 6.67% | 34.0 | 34.0 |
| 34.0 | 34.0 | 0.34 | 6.25% | 33.0 | 33.0 |
| 36.0 | 36.0 | 0.36 | 5.88% | 32.0 | 32.0 |
| 38.0 | 38.0 | 0.38 | 5.56% | 31.0 | 31.0 |
| 40.0 | 40.0 | 0.4 | 5.26% | 30.0 | 30.0 |
| 42.0 | 42.0 | 0.42 | 5.00% | 29.0 | 29.0 |

All gears described herein are metric, with a selected Module of one. For this fixed planet carrier design, the gear ratio is the ratio of each respective sun gear pitch diameter to the constant pitch diameter of the internal ring gear. Speed ratio refers to the reduction in speed between successive planetary gear assemblies. Other methods of altering the rotational speed of the dynamic phantom are equally acceptable, such as changing the pitch diameter of the sun and planet gears accordingly, or varying the speed of the drive-shaft.

Figure 3:
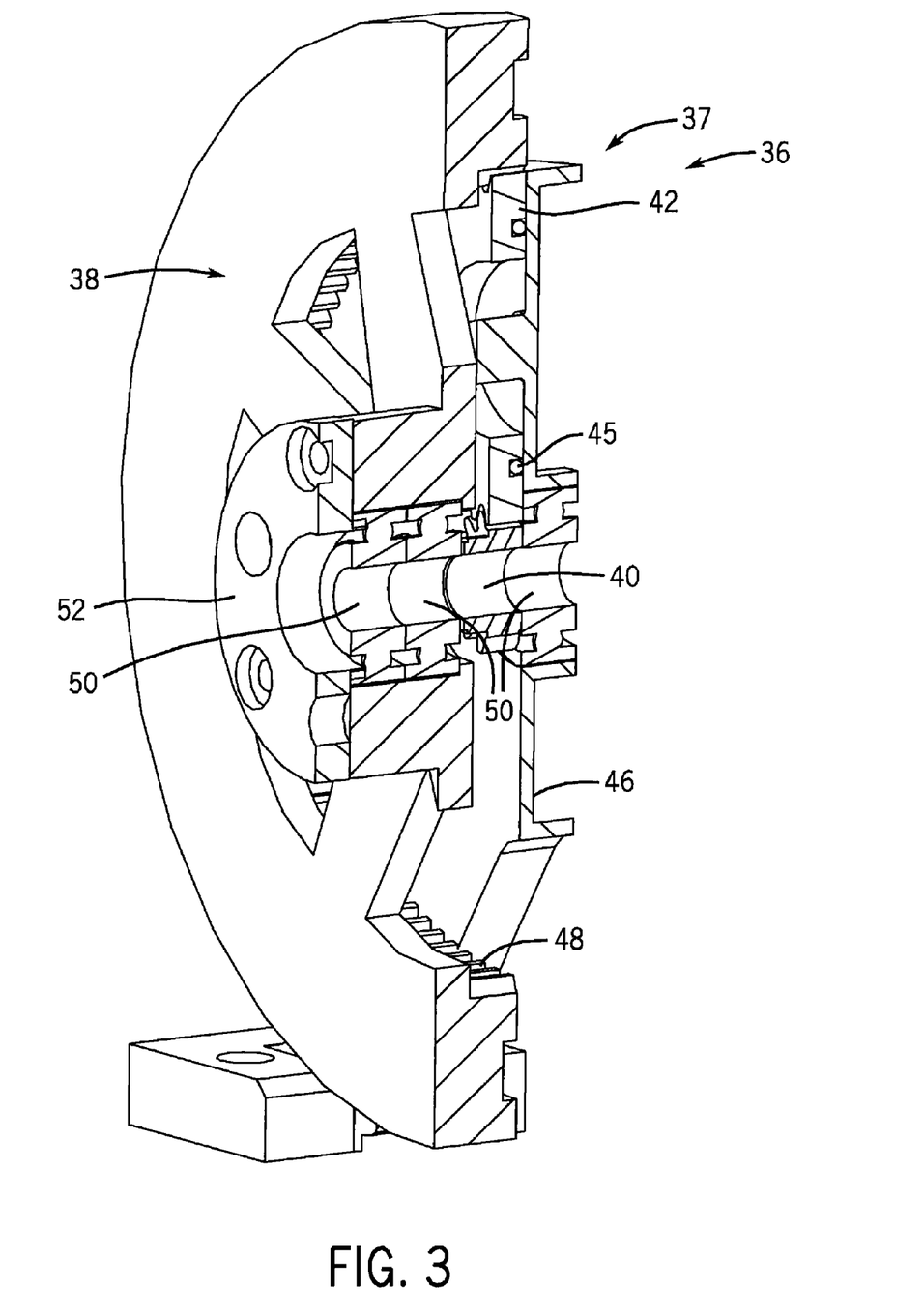
FIG. 3 is a cross-sectional view of a single planetary gear assembly, in accordance with the present invention.

Referring now to FIG. 3, a cross-section of a planetary gear assembly in a free-standing configuration 36 has had the above-described large diameter bearing that is integral with the internal ring gear removed and replaced with a smaller bearing set 37 whose inner ring(s) rides on the drive shaft (not shown), and whose outer ring(s) support an internal ring gear 38 in order to lower cost and part count. Each successive internal gear 38 is mounted on its own separate single-planet-gear drive train. Specifically, a sun gear 40 is driven by a drive shaft (not shown) in a manner described above.

A planet gear 42 is mounted on a support 46. The planet gear 42 is driven by the sun gear 40. An internal ring gear 48 is driven by the planet gear 42. Bearings 50 for the internal gear are mounted in a back-to-back configuration to provide moment support for the internal ring gear using spacers. Plastic ball bearings, such as those available from KMS Bearing under Part number A606-P, may be used. Concentricity of the internal gear 38 and the drive shaft driving the sun gear 40 is obtained through the use of plastic conrad-type ball bearings. As a result, only one spur-toothed planet gear 42 is needed for power transmission. The planet gear 42 need only be supported by only one deep groove (Conrad) bearing 45 or, alternatively, a plastic needle roller bearing or a journal bearing because the gear tooth forces are in the same plane as the bearing support 45. Note that if helical gears are used for smoother velocity transmission, two or three planet gears would be needed so as to prevent a moment from being placed on the internal gear which would be caused by the thrust forces generated by the helical gears. An internal gear bearing preload cover 52 is used to enclose the bearings 50 and pre-load the inner races.

The axial spacing of the bearings 50 that support the internal ring gear is small in relation to the diameter of the ring gear 48. Although this could possibly lead to some tilt error motion of the ring gear 48 and any slotted disk that is mounted to it, any motion would be in a non-sensitive direction with respect to the measurement of an imaging device's temporal resolution.

The need for very precise velocity control of the motor driving the drive shaft is preferable due to the fact that small variations in the velocity of the gears during data collection could cause variations in the modulation data. Other embodiments of the apparatus can include closed loop velocity control and recordation of the servo error to more accurately monitor the rotation rate of the gear assemblies and its effect on the characterization of an imaging device. As noted, in one embodiment, the rotation rate of the planetary drive-shaft during data acquisition was approximately 10 RPM, although other speeds are also practical.

Figure 4:
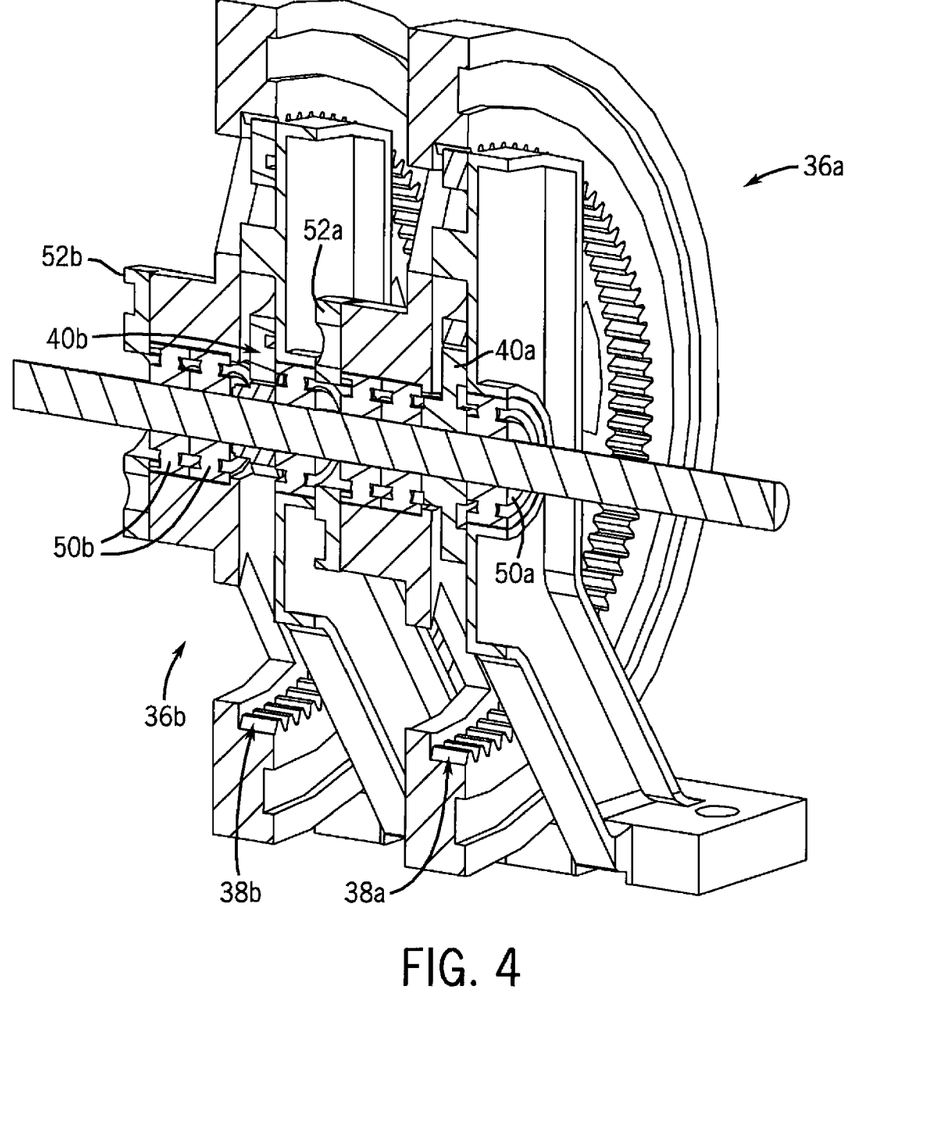
FIG. 4 is a perspective cross-sectional view of one embodiment of a system for characterizing temporal resolution in accordance with the present invention that includes two planetary gear assemblies like that illustrated in FIG. 3 and having a common drive shaft.

Referring to FIG. 4, it is contemplated that two gear assemblies 36a, 36b may advantageously be utilized. The assemblies 36a, 36b are preferably manufactured using stereo-lithography (SLA) rapid-prototyping. However, other methods such as machining, injection molding, and casting could be used for higher volume manufacture and for long term dimensional stability. The planetary gear assemblies 36a, 36b have two different sun gear sizes. A 16 tooth (16 mm pitch diameter) sun gear may be desirable for one sun gear 40a because it is one of the smallest gears with well-formed teeth that can be mounted on an 8 mm drive shaft. A 34 tooth (34 mm diameter) sun gear may be desirable for the other sun gear 40b so as to achieve a readily discernable difference in the speeds between the two gear assemblies 36a, 36b.

Another constraint that may be considered when choosing gear ratios is the diameter of the drive shaft. In the illustrated embodiment, an 8 mm diameter shaft is desirable because it enables a relatively small sun gear to be used, while still providing enough stiffness to support the desired spacing of the planet 42 and internal gear 38. A drive shaft diameter of 8 mm can accommodate a bearing spacing of up to 80 mm based on Saint Venant's principle, while controlling angular errors of mounted components.

Each internal ring gear 38a, 38b includes a slotted disk (not shown in FIG. 4) supported thereon. Specifically, referring to FIGS. 5 and 6, exemplary slotted disks 56, 58 are illustrated. As will be described below, each slotted disk 65, 58 has several rings, each at different radii, with each ring having a selected number of equally spaced slots in order to simulate a desired, predetermined frequency. The use of slotted disks allows for the collection of several different frequency data sets at once.

Figure 5:
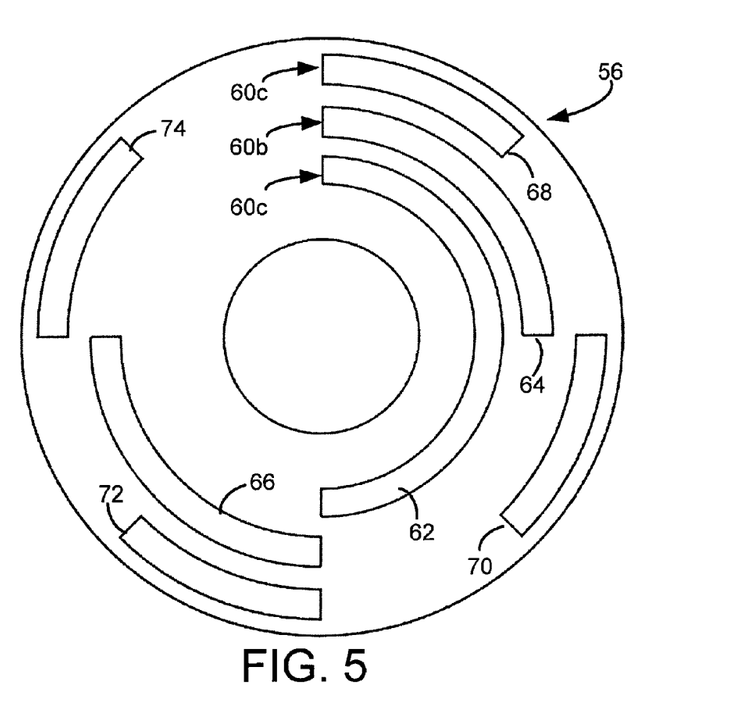
FIG. 5 is a plan view of a disk for use with the systems of FIGS. 1-4, in accordance with the present invention.

In particular, referring to FIG. 5, the slotted disk 56 is designed to be driven by the sun gear 40a of the first gear assembly 36a, which may have a 34 tooth sun gear. The slotted disk 56 typically includes three circularly arranged sets of slots 60a, 60b, 60c, or slotted rings, each slotted ring at a different radial distance. The inner most ring 60a includes a single slot 62, the middle ring 60b includes two equally spaced slots 64, 66, and the outer most ring 60c typically includes four equally spaced slots 68, 70, 72, 74.

As described above, for CT imaging systems, the slots 60a, 60b, 60c are advantageously hollow to provide a very distinct contrast between the disk 56 (preferably made of plastic-type material) and the slots 60a, 60b, 60c (preferably composed of empty space) when imaged using x-rays. However, when using the system with other imaging modalities, such as MRI systems, it may be advantageous to select the materials forming the disk 56 and slots 60a, 60b, 60c so as to provide a significant contrast variation between the two materials when imaged using the MRI system. For example, it may be advantageous to form the disk 56 from a material that has properties similar to dense tissue (e.g., a particular polymer) and to fill the slots 60a, 60b, 60c with a material, such as water, that provides an Nuclear MR signal that can be readily weighted by the MRI system during reconstruction to provide a significantly different contrast from that of the disk 56. It should be appreciated that the foregoing is but one example of how a dynamic phantom having at least two distinct contrast areas may be formed. Any suitable combination of materials and configurations may be utilized and the specific combination of materials and configurations may vary significantly based on modality and specific configuration of a given imaging device.

Figure 6:
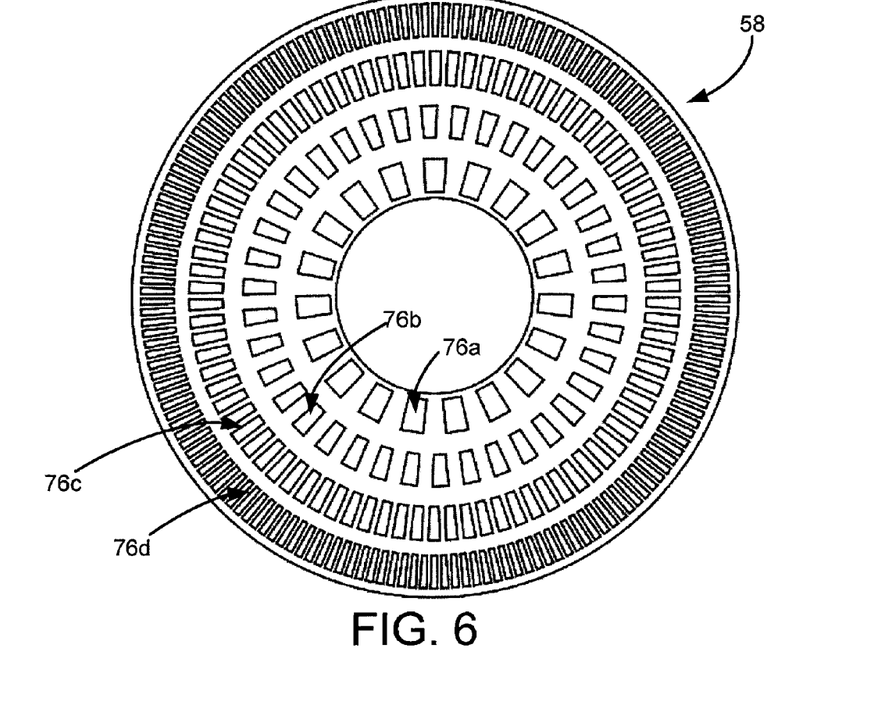
FIG. 6 is a plan view of another disk for use with the systems of FIGS. 1-4, in accordance with the present invention.

Referring now to FIG. 6, the slotted disk 58 is designed to be driven by the sun gear 40b of the second gear assembly 36b, which may have a 16 tooth sun gear. The slotted disk 58 includes four slotted rings 76a, 76b, 76c, 76d having 19, 38, 75, and 150 slots, respectively. The slots formed in each ring 76a, 76b, 76c, 76d are uniform in size and shape. The specific number of slots per ring 76a, 76b, 76c, 76d is dependant upon the desired frequency of the dynamic feature and the rotational velocity of the internal gear supporting it.

By rotating the slotted disks 56, 58, dynamic features with distinct frequencies are generated by each set of rotating slots arranged at varying radial distances and having varying numbers of slots at each ring. In particular, in the disk 56 illustrated in FIG. 5, the first, innermost ring 60a is designed to generate a dynamic feature having a frequency of 0.0625 Hz. Similarly, the second ring 60b generates a dynamic feature having a frequency of 0.125 Hz and the third ring 60c generates a dynamic feature having a frequency of 0.25 Hz. Similarly, the disk 58 illustrated in FIG. 6 is designed to generate a dynamic feature having a frequency of 0.5 Hz from the first, innermost ring 76a. Additionally, the second ring 76b generates a dynamic feature with a frequency of 1 Hz, the third ring 76c generates a dynamic feature with a frequency of 2 Hz, and the fourth, outermost ring 76d generates a "dynamic feature" at a frequency of 4 Hz.

This range of frequencies is but one example that may be chosen to encompass a common range of frequencies seen in physiological events. For example, a human heart, an oft-imaged organ, can beat with a frequency ranging from below 0.5 Hz, or 30 beats per minute, to above 4 Hz, or 240 beats per minute. Even higher frequencies are possible under pathologic conditions such as atrial99 or ventricular fibrillation.

Accordingly, an imaging plane can be selected that is transverse to the two parallel disks 56, 58 arranged in the respective gear assemblies 36a, 36b of FIG. 4. By rotating the disks, regions in the imaging plane are affected by the dynamic feature formed by the movement of the slots. These physical properties of these regions are changed as the dynamic feature is generated by the spinning disks 56, 58 with the slots arranged at constant radii. Using two stages of gear assemblies 36a, 36b, as illustrated in FIG. 4, and the slotted disks 56, 58, as illustrated in FIGS. 5 and 6, allows the generation of dynamic features corresponding to a wide range of frequencies, and allows the dynamic features to be positioned close together near the isocenter 14 of the imaging device 12 of FIG. 1.

The specific number, size, and spacing of the slots can be determined as a function of the rotational speed of each internal gear. One analysis includes increasing the drive shaft speed in increments of 10 RPM through successive iterations.

The steps of the analysis for a drive shaft speed of 10 RPM are shown in Tables 3a, 3b, 3c and 3d. The first step is to calculate the frequency at which the internal gears rotate, as seen in Table 3a. In the table, "IG" refers to the internal ring gear, and the gear ratio refers to that between the specified sun gear and the internal ring gear, which has a constant pitch radius for both instances.

TABLE 3a

Calculating Internal Gear Frequency

| Parameter | Value | Units |
|---|---|---|
| Shaft Speed | 10 | Rpm |
| Gear Ratio - 16 | 0.16 | — |
| IG 1 Speed | 1.6 | Rpm |
| IG 1 Frequency | 0.03 | Hz |
| Gear Ratio - 34 | 0.34 | — |
| IG 2 Speed | 3.4 | Rpm |
| IG 2 Frequency | 0.06 | Hz |

Furthermore, two or more disks with multiple slots could be attached to a single ring gear to obtain even greater dynamic range.

The next step is to determine the number of slots necessary to generate dynamic features with a desired frequency. As described above, each rotating ring includes a plurality of slots and generates a dynamic feature corresponding to a region in an imaging plane, with each dynamic feature varying in time at a corresponding known frequency. In other words, as the slotted disk rotates through an imaging plane, an event pair is created as a slot (for example, containing air or another substance) that passes through the imaging plane followed by a region made up of disk material (for example, plastic). The desired number of slots is calculated by dividing the desired dynamic feature frequency by the frequency of rotation of each disk. Table 3b shows a calculation of the number of slots necessary to simulate a desired frequency on each respective planetary gear assembly. At certain frequencies, it is infeasible to achieve the desired frequencies using an integer number of slots. As a result, the integer number of slots that results in the closest frequency to that desired is used.

TABLE 3b

Calculating Number of Slots

| Desired Frequency (Hz.) | Number of Slots | |
|---|---|---|
| | 16 tooth gear Stage | 34 tooth gear Stage |
| 4 | 150 | 70.59 |
| 2 | 75.000 | 35.29 |
| 1 | 37.500 | 17.65 |
| 0.5 | 18.750 | 8.82 |
| 0.25 | 9.375 | 4.41 |
| 0.125 | 4.688 | 2.21 |
| 0.0625 | 2.344 | 1.10 |
| 0.03125 | 1.172 | 0.5515 |

Table 3c shows an actual frequency achieved using a given number of slots and a resultant error compared to a desired frequency of 4, 2, 1, ½, ¼, ⅛, and ¹⁄₁₆ Hz respectively.

TABLE 3c

Frequency Error Analysis

| Integer No. of Slots | | Actual Frequency | | |
|---|---|---|---|---|
| N tooth gear stage | | | | |
| 16 Tooth | 34 Tooth | 16 Tooth | 34 Tooth | Percent Error |
| 150.00 | | 4.00 | | 0% |
| 75.00 | | 2.00 | | 0% |
| 38.00 | | 1.01 | | 1% |
| 19.00 | | 0.50667 | | 1% |
| | 4.00 | | 0.227 | −10% |
| | 2.00 | | 0.1133 | −10% |
| | 1.00 | | 0.0567 | −10% |

Furthermore, table 3d shows a calculation performed in order to determine the required arc length of each slot. The total arc length includes that of the slot, and the corresponding section of disk material that create an event pair when taken as a unit. The slot spacing column in Table 3d refers to the distance from the beginning of one arc-shaped slot to the next in degrees. A large hole in the middle of each disk is used to mount it to an internal ring gear.

TABLE 3d

Slot Size (arc length) Calculations

| Circle | 360 | Degrees |
|---|---|---|
| 10 RPM Shaft Speed | | |
| Number of Slots | Slot Size | Slot Plus Spacing |
| 150 | 1.200 | 1.200 |
| 75.00 | 2.400 | 2.400 |
| 38.00 | 4.736 | 4.736 |
| 19.00 | 9.474 | 9.474 |
| 4.00 | 45.000 | 45.000 |
| 2.00 | 90.000 | 90.000 |
| 1.00 | 180.000 | 180.000 |
| 0.50 | 360.000 | 360.000 |

Drive shaft speed also affects the output frequency of each dynamic feature. Table 4 shows the results of further analysis for drive shaft speeds of 20 and 40 RPM. As a result of the increase in speed, the slot sizes required to simulate slower frequencies increase to unobtainable values. Note that as the drive shaft speed is increased, the number and size of the slots needed to simulate small frequencies, such as ¹⁄₁₆ Hz, increases dramatically.

TABLE 4

Calculation of slot arc length for driveshaft speeds of 20 and 40 RPM

| 20 RPM Shaft Speed | | |
| --- | --- | --- |
| Number of Slots | Slot Size | Slot Plus Spacing |
| 75 | 2.400 | 2.400 |
| 38.00 | 4.737 | 4.737 |
| 19.00 | 9.474 | 9.474 |
| 9.00 | 20.000 | 20.000 |
| 2.00 | 90.00 | 90.00 |
| 1.00 | 180.00 | 180.00 |
| 0.50 | 360.00 | 360.00 |
| 0.25 | 720.00 | 720.00 |
| 40 RPM Shaft Speed | | |
| Number of Slots | Slot Size | Slot Plus Spacing |
| 38 | 4.800 | 4.800 |
| 19.00 | 9.474 | 9.474 |
| 10.00 | 18.000 | 18.000 |
| 5.00 | 36.000 | 36.000 |
| 1.00 | 180.00 | 180.00 |
| 0.50 | 360.00 | 360.00 |
| 0.25 | 720.00 | 720.00 |
| 0.13 | 1440.00 | 1440.00 |

The highlighted rows above denote a configuration where the sum of the arc length of the slot and the required arc spacing between each cut is larger than 360 degrees, and hence impossible to create as a single planar constant radius arc cut.

Figure 7:
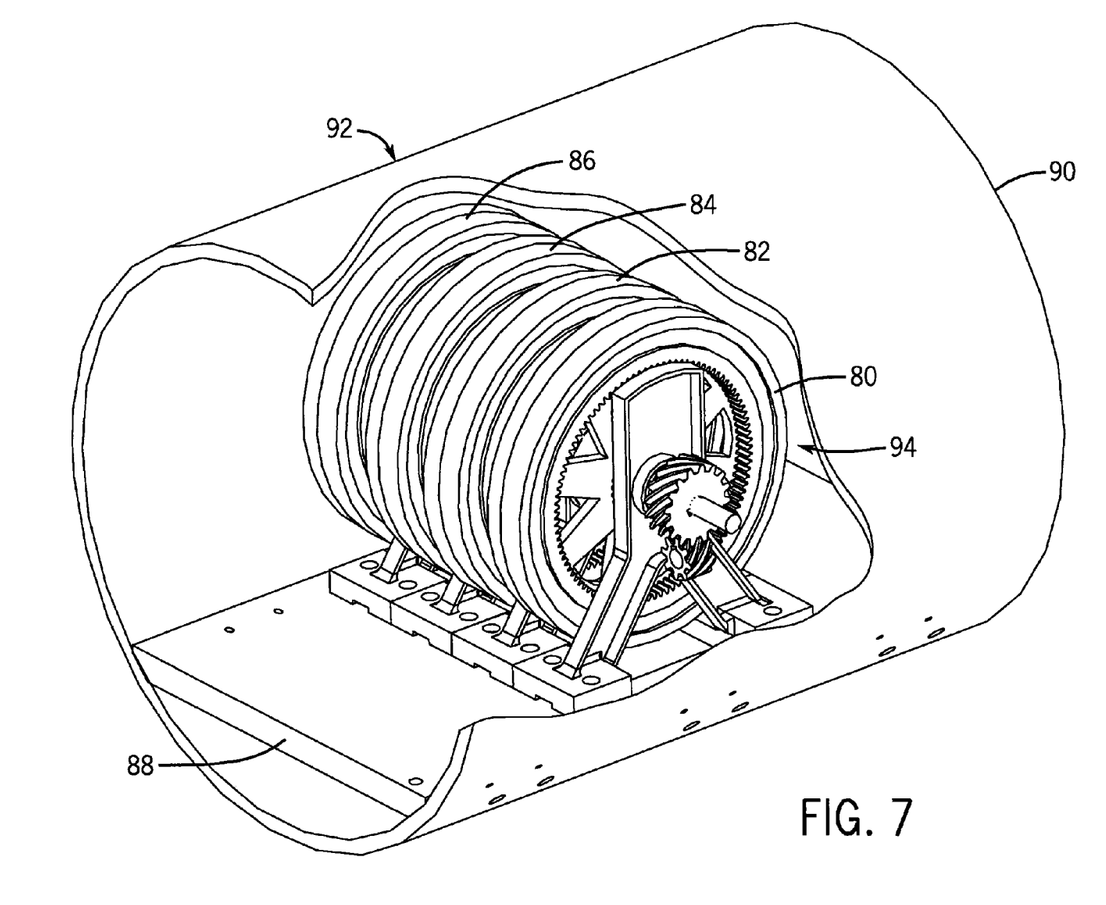
FIG. 7 is a perspective view of the systems of FIGS. 1-6 incorporated into a static, phantom system.
Figure 8:
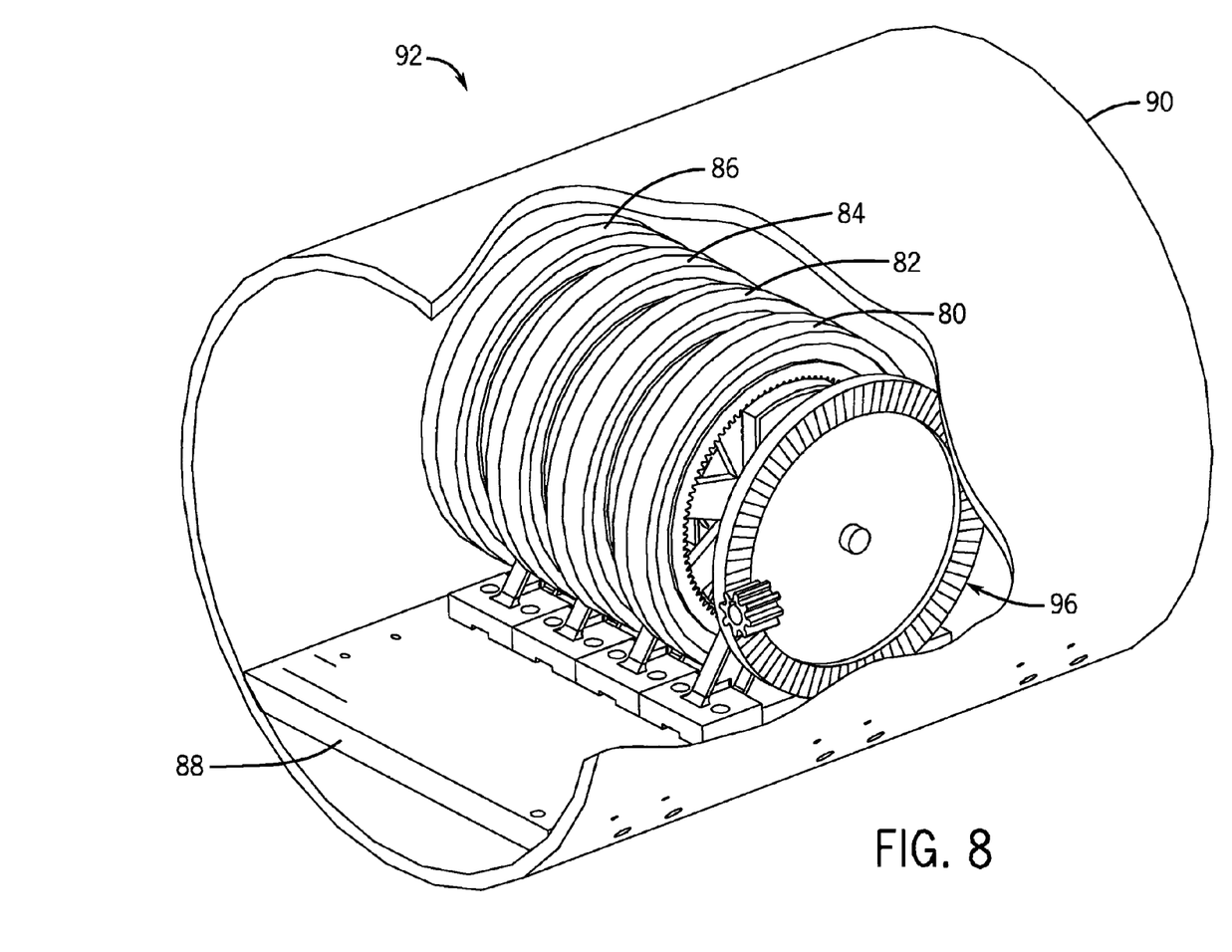
FIG. 8 is another perspective view of the system of FIG. 7 in a reversed orientation.

Referring now to FIGS. 7 and 8, it is contemplated that the above-described system may be configured to have a shape similar to a standard, static phantom. In the illustrated configuration, four planetary gear assemblies and associated disks 80, 82, 84, 86 have been arranged on a mounting platform 88 in a large-bore plastic cylinder 90 so that the moving parts of the machine are shielded from the surrounding environment. In FIG. 7, the pitch diameters of the helical gears 94 of the overall CT calibration tool, generally designated 92, mounted in the cylindrical shell 90 are visible. On the other hand, in FIG. 8, the face gears 96 have been added.

Figure 9:
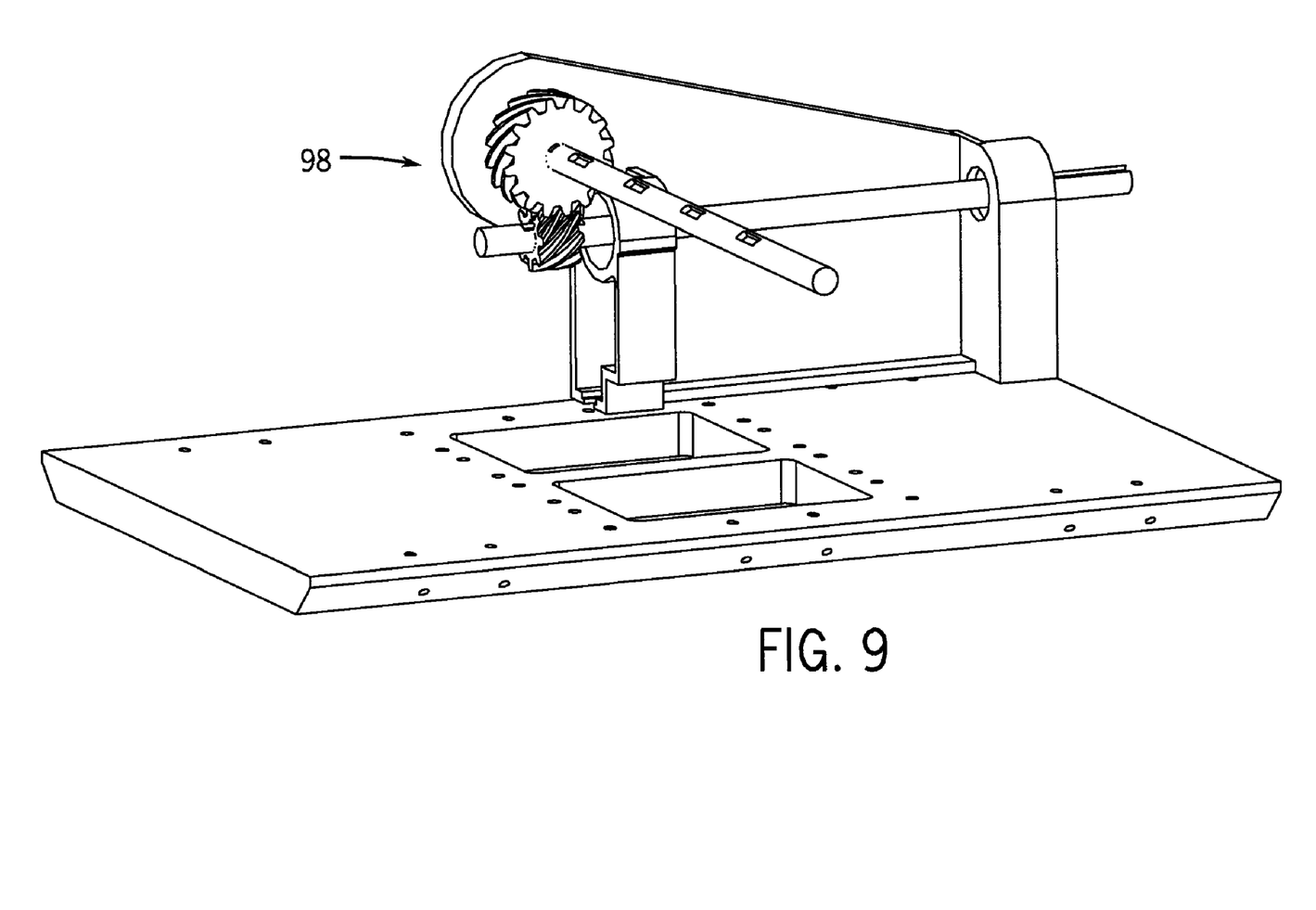
FIG. 9 is a perspective view of the motor coupling used to connect an output shaft of a motor to a driveshaft through bevel gears used to drive the present invention.

In accordance with one embodiment, referring to FIG. 9, a set of beveled gears 98 arranged may be used to drive the planetary gear assemblies 80-86 of FIGS. 7 and 8. However, when using a significant number of gear assemblies, such as four in the embodiment illustrated in FIGS. 7 and 8, in order to achieve a larger range of simulated frequencies, the available volume within the cylinder 90 became very limited, based on the scanning volume capabilities of the scanner. In this case, the bevel gear assembly 98 may be too large to fit inside of the cylinder 90. In this case, alternative types of gears for a right-angle gearbox that may be used include helical gears, face gears, and spiral bevel gears, and the like. When deciding on the specific type of gear train to use for a particular embodiment, properties such as torque transmission, accuracy of velocity transmission, and the volumetric profiles of the gear assembly with respect to manufacturing cost should be considered.

In the embodiment shown in FIG. 9, a gearbox is used to allow the motor to be placed outside of the scanning volume. In addition, it is contemplated that the motor can be driven by a microcontroller, which communicates with a computer (not shown).

Figure 10:
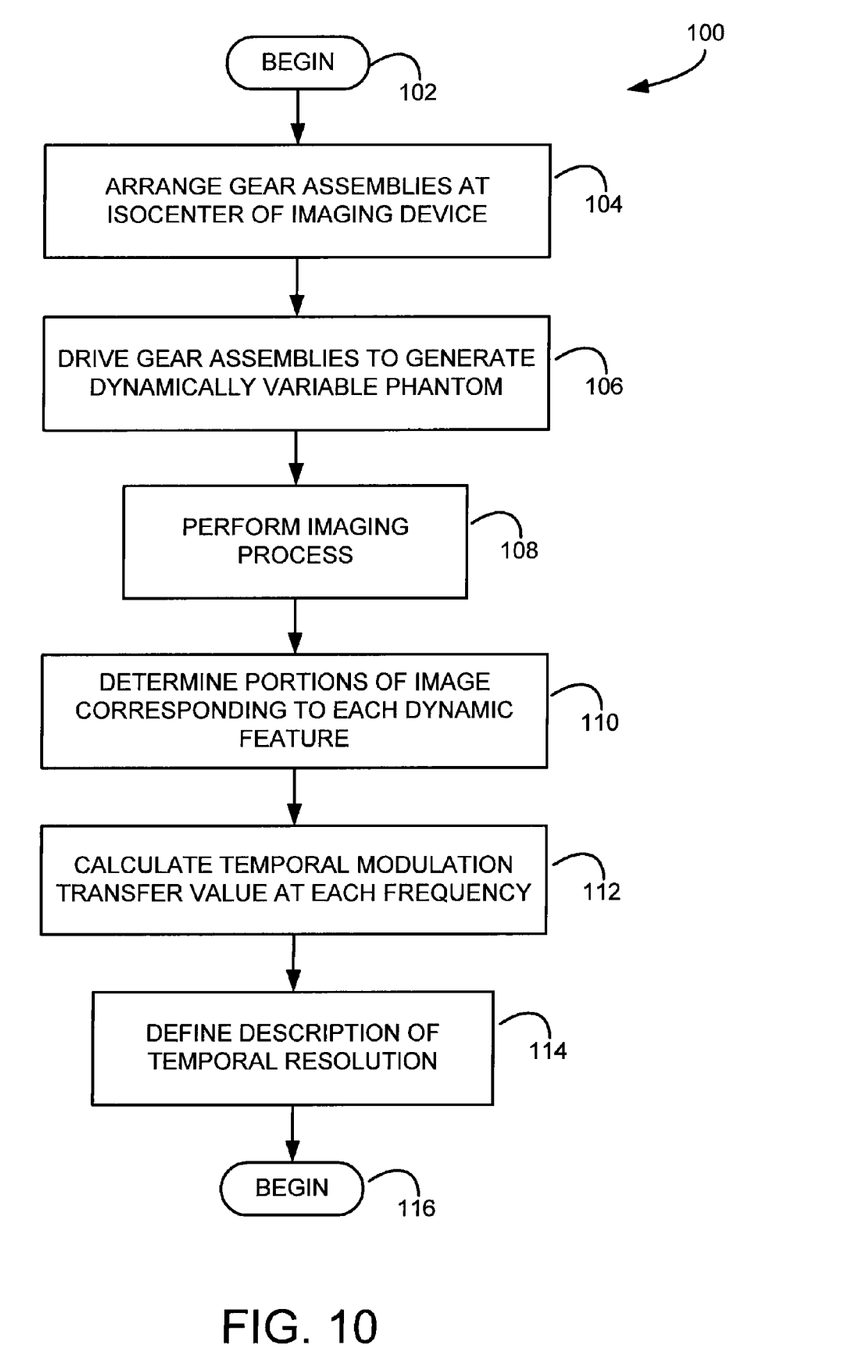
FIG. 10 is a flow chart setting forth the steps of a method for determining a temporal modulation transfer function of an imaging system using the above-described systems in accordance with the present invention.

Referring now to FIG. 10, a method 100 for using the above-described system to determine the t-MTF of an imaging device at a set of specified frequencies begins 102 by placing a system for characterizing temporal resolution, including the gear assembly or assemblies at or near the isocenter of the imaging device at process step 104. Using currently available laser-based object positioning systems, the cylindrical shell design of the system described above with respect to FIGS. 7 and 8, aids the user in arranging the system at the optimal position, achieving as close to a vertical orientation of the disks as possible, taking into account human error.

Driven by the motor, the gear assembly rotates to create a dynamic phantom at process block 106. Specifically, rotating the gear assemblies generates a plurality of dynamic features each having a known specified frequency. The process continues by performing an imaging process of the selectable imaging plane within which the rotating gears are located at process block 108. The resulting image data is then analyzed using a computer or other processor to first determine the portions of the image data corresponding to each dynamic feature at process block 110, and then calculate a temporal modulation transfer value at each of the specified frequencies at process block 112.

In one example, a series of ten different images is obtained. The image data making up these images is analyzed by a computer, using for example Matlab. In this example, version 7.0.4 of Matlab was used. Image data corresponding to each of the frequencies in the desired set of frequencies is analyzed to determine an average gray scale value for the corresponding imaged dynamic feature. For example, the following table shows the grayscale image data generated using the Matlab script:

TABLE 5

| Grayscale Data. | | | | | | | | | |
| --- | --- | --- | --- | --- | --- | --- | --- | --- | --- |
| 4 Hz | 745 | 734 | 736 | 747 | 752 | 751 | 747 | 746 | 750 | 752 |
| 2 Hz | 760 | 780 | 756 | 735 | 710 | 718 | 730 | 727 | 721 | 710 |
| 1 Hz | 593 | 641 | 679 | 704 | 736 | 712 | 709 | 715 | 722 | 736 |
| ½ Hz | 1080 | 714 | 848 | 705 | 808 | 853 | 781 | 823 | 762 | 808 |
| ¼ Hz | 34 | 231 | 621 | 743 | 595 | 502 | 491 | 605 | 661 | 595 |
| ⅛ Hz | 25 | 143 | 567 | 780 | 905 | 758 | 687 | 778 | 849 | 905 |
| 1/16 Hz | 1245 | 1282 | 855 | 644 | 515 | 637 | 734 | 642 | 572 | 515 |

To calculate a temporal modulation transfer value at each of the specified frequencies at process block 112, then values of temporal modulation transfer (or simply "modulation") can be calculated as follows.

Let OI1 and OI2 denote the observed intensities of regions 1 and 2 respectively in the dynamic phantom. In the above implementation of this temporal resolution phantom (TRP) for CT, OI1 and OI2 will correspond to the observed grayscale or Hounsfield units of the air in the slot and the intervening plastic between the slots, respectively. Let EI1 and EI2 represent the expected intensity values in the contrast regions in which the TRP was not moving. In other words, OI1 and OI2 represent the intensity values in the dynamic condition while EI1 and EI2 represent the values in the static situation. The difference between the observed and the expected values is solely because of the motion of the slots. The Modulation Transfer is defined as:

Modulation=(OI1−OI2)/(EI1−EI2)  Eqn. 2.

In the above formula, OI and EI are modality independent. This equation states that the modulation at a given frequency is calculated by finding the maximum range of signal intensity values for that frequency over the dynamic feature generating that frequency, and then dividing by the difference between expected values in the static condition. In the above example, OI1=1282.1, and OI2=25.403. Table 6 shows the resulting modulation values for the given frequency set.

TABLE 6

Modulation values for exemplary frequency set

| Frequency (Hz) | Range | Modulation |
|---|---|---|
| 0.0625 | 767.01 | 0.810 |
| 0.125 | 879.13 | 0.700 |
| 0.25 | 708.42 | 0.564 |
| 0.5 | 374.31 | 0.298 |
| 1.0 | 143.43 | 0.114 |
| 2.0 | 69.66 | 0.055 |
| 4.0 | 18.48 | 0.015 |

To define a temporal modulation transfer function, let "I" denote a tomographic imaging device that is capable of repeatedly imaging a volume V(x, y, z, t) with a time period T. Using I, a volume V can be rendered as a discrete sequence of the volumes $V_0, V_1, V_2, \ldots V_n$, where each $V_i$ is a measurement of V using the device I in the time interval t=[i, i+1]. Assuming that the temporal response of the system is space invariant, the designation of the spatial location (x, y, z) can be dropped from the description of the imaging volume V. Accordingly, the imaging volume V can now be described simply as V(t). The temporal modulation transfer function is a measurement of the fidelity with which the temporal behavior of a pixel or voxel in the plane or volume being imaged is captured by the imaging device I.

The modulation of a time-varying function is defined as the amplitude of the principle frequency in a function. Let V(t, f) be a time-varying square wave with a frequency f, and let I(V(t, f)) denote the time varying image of V(t, f). Hence, the temporal MTF of I is defined as:

$$t-MTF(f) = \frac{\text{modulation}[I(V(t, f))]}{\text{modulation}[V(t, f)]}.$$  Eqn. 3

Here, the modulation[I(V(t,f))] measures the absolute variation in the amplitude of V(t, f) and the modulation transfer is the fraction of the modulation of V(t, f) that is transferred in the image.

This temporal modulation transfer value versus frequency information is then analyzed to determine temporal resolution at process block 114 defined, for example, as a frequency at which the temporal modulation transfer falls below a predetermined threshold or percentage, such as 10%.

Figure 11:
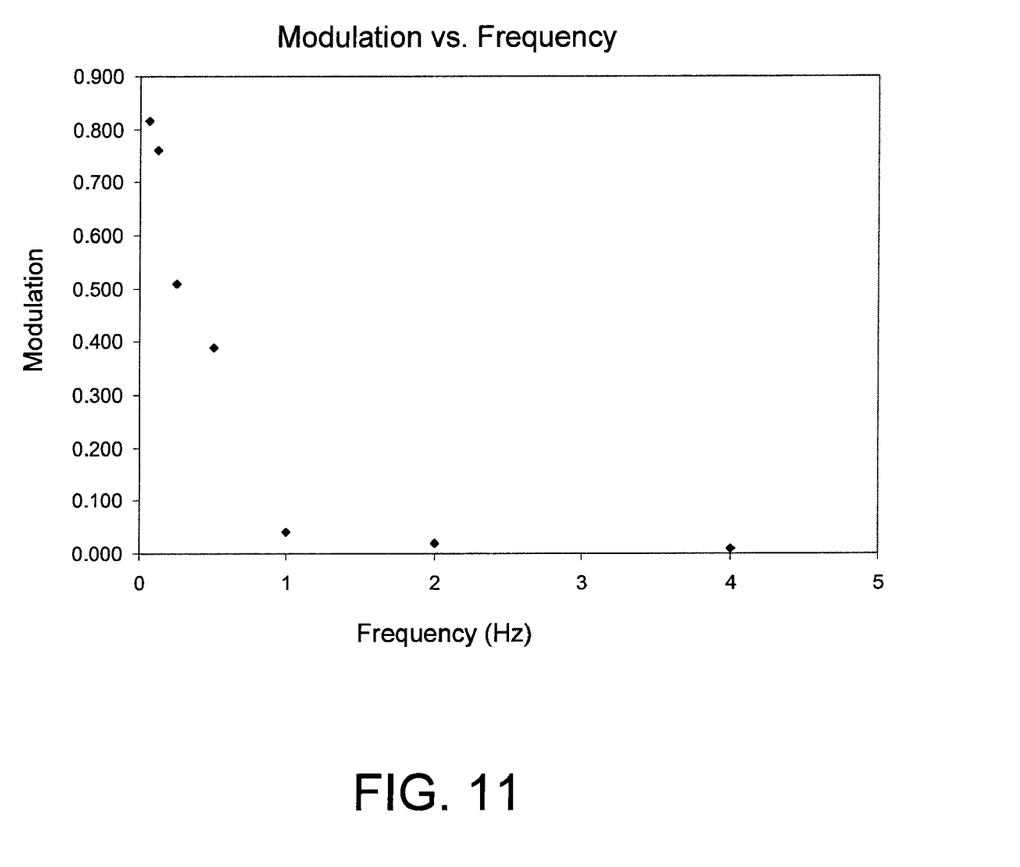
FIG. 11 is a graph of modulation versus frequency for an exemplary imaging device.

Specifically, a plot of temporal modulation transfer versus frequency for the present example is shown in FIG. 11. The decay of the modulation as the signal frequency is increased is apparent. From FIG. 11, the temporal resolution, defined in this example as the frequency where the modulation is 0.10, is at approximately 1.5 Hz using a straight line fit of the data. Other data fits can also be performed. This concludes the process 116.

Preferred embodiments of the apparatus should meet the following functional requirements. If the apparatus is to be used with a CT imaging device, it should be fabricated primarily using plastic material, in order to have low X-ray attenuation characteristics. If it is to be used with a MR imaging device, it should be fabricated using an MR-compatible material. The apparatus should be capable of simulating dynamic features over a large range of input frequencies (speeds), with the appropriate range depending on the type of imaging device being characterized. Accurate speed differentials should be obtainable using planetary gear assemblies, wherein multiple assemblies can be driven by one shaft. Although not required, an internal gear is preferably a common part among all assemblies in order to minimize cost, and provide a structure on which to mount the disks that generate the dynamic features. The apparatus should have a small volume and profile, such that it fits in the scanning volume of the imaging device.

It is also envisioned that the apparatus be located at different points on a grid around the isocenter in order to map the sensitivity of the imaging device with respect to position within the imaging volume. For example, the apparatus could be mounted to an XYZ positioning device and moved to obtain image data according to various positions.

The described apparatus is advantageous in that conventional planetary gear assemblies are low cost, can be easily manufactured, and are good at precision velocity transmission. Successive generations of the apparatus could utilize helical gears, and the axial forces generated could also act to help preload the plastic ball bearings. Since this apparatus is driven at relatively low constant speed with no external loads, the teeth of the gears were chosen to enable ease of manufacturing, such as by rapid prototyping, although other ratios are also possible.

The present invention has been described in terms of the various embodiments, and it should be appreciated that many equivalents, alternatives, variations, and modifications, aside from those expressly stated, are possible and within the scope of the invention. Therefore, the invention should not be limited to a particular described embodiment.

The invention claimed is:

1. A method for determining a temporal resolution of an imaging device, the method comprising:
   placing an apparatus configured to create dynamically variable imaging features near the isocenter of the imaging device;
   driving the apparatus to produce a plurality of dynamic features each having a known, specified frequency;
   imaging the dynamic features with the imaging device to produce image data; and
   analyzing the image data corresponding to the dynamic features to determine a temporal modulation transfer value at each of the known specified frequencies.

2. The method of claim 1 further comprising utilizing a temporal modulation transfer function (t-MTF) to calculate the temporal modulation transfer values for each dynamic feature according to:

$$t-MTF(f) = \frac{\text{modulation}[I(V(t, f))]}{\text{modulation}[V(t, f)]};$$

wherein "I" denotes a tomographic imaging device that is capable of repeatedly imaging a volume V(x, y, z, t) with a time period t, V(t,f) is a time-varying signal with a frequency f, and I(V(t,f)) denotes the time varying image of V(t,f), such that the modulation[I(V(t,f))] corresponds to an absolute variation in an amplitude of V(t,f) such that the modulation transfer function is a fraction of a modulation of V(t,f) that is transferred in an image of the apparatus by the imaging device.

3. The method of claim 1 further comprising analyzing the temporal modulation transfer values, and comparing them to their respective signal frequencies to determine a value for temporal resolution, defined as a frequency at which the temporal modulation transfer value for a signal falls below a predetermined percentage.

4. The method of claim 1 wherein modulation at a given frequency is calculated by finding the modulation in the signal intensity values for the given frequency across multiple images of the apparatus by the imaging device, and dividing the observed modulation (i.e., the difference between maximum and minimum signal intensity values across the multiple images of the apparatus produced by the imaging device) by an expected maximum and minimum intensity values imaged by the device during a scan.

5. The method of claim 1 further comprising moving the apparatus from the isocenter of the imaging device and repeating the steps of driving the apparatus to produce a plurality of dynamic features each having a known, specified frequency, imaging the dynamic features with the imaging device to produce image data, and analyzing the image data corresponding to the dynamic features to determine a temporal modulation transfer value at each of the known specified frequencies.

6. The method of claim 1 wherein driving the apparatus includes moving a phantom having at least two distinct contrast areas formed therein in a predetermined pattern.

7. The method of claim 6 wherein driving the apparatus includes rotating a gear assembly using a motor to move the phantom in a predetermined rotational pattern to create the dynamic features.

8. The method of claim 7 wherein rotating the gear assembly includes rotating a planetary gear assembly including a sun gear driven by the drive shaft to thereby rotate a planet gear driven by the sun gear, a ring gear driven by the planet gear, and a slotted disk is mounted to the ring gear.

9. A system for characterizing a temporal resolution of an imaging device, the system comprising:
a drive shaft configured to be driven by a motor;
a gear assembly configured to be driven by the drive shaft; and
a phantom composed of at least two materials to provide distinct contrast in a reconstructed image, and wherein the phantom is configured to be moved by the gear assembly to thereby create at least one dynamic feature for imaging by the imaging device.

10. The system of claim 9 wherein the gear assembly includes a planetary gear system configured to drive the phantom.

11. The system, of claim 10 wherein the planetary gear system includes a sun gear driven by the drive shaft, at least one planet gear driven by the sun gear, and a ring gear driven by the at least one planet gear, and wherein each gear may include at least one of a spur and helical gear tooth configuration.

12. The system of claim 11 wherein the phantom includes a disk attached to the ring gear such that it rotates as the ring gear rotates.

13. The system of claim 12 wherein the disk includes a plurality of features arranged as a pattern spaced around the disk.

14. The system of claim 13 wherein the features are comprised of at least one different material than the disk.

15. The system of claim 14 wherein the material of the disk and the material of the features are selected to be viewable in an image, generated using a medical tomographic imaging device, as having separate, distinct contrasts.

16. The system of claim 13 wherein the plurality of features are arranged to form a plurality of rings of features arranged at varying radii about the disk.

17. The system of claim 13 wherein rotation of the disk causes the plurality of features to rotate at a known frequency to thereby create a plurality of dynamic features having known frequencies.

18. The system of claim 9 further comprising:
a plurality of gear assemblies configured to be driven by the drive shaft; and
a plurality of phantoms composed of at least two materials configured to provide distinct contrast in a reconstructed medical image and configured to be moved by respective gear assemblies to thereby create a plurality of dynamic features for imaging by the imaging device.

19. The system of claim 18 wherein each of the plurality of phantoms includes features arranged in rings about a disk, each ring having a corresponding radius different than others to form a pattern of features, such that when the disk rotates at a constant velocity, a plurality of dynamic features are produced by each disk, each dynamic feature having a corresponding known frequency.

20. The system of claim 9 wherein movement of the phantom causes the at least two materials to move at a known velocity, to thereby create the at least one dynamic feature, having known frequency, when imaged by the imaging device.

21. The system of claim 20 further comprising at least one processor configured to perform an imaging process using the imaging device to produce imaging data having information about the at least one dynamic feature gathered using the imaging device and analyze the imaging data corresponding to the at least one dynamic feature to determine temporal modulation transfer values for the at least one dynamic feature, having a specified frequency.

22. The system of claim 21 wherein the at least one processor is further configured to compare the temporal modulation transfer values of each dynamic feature against the frequency of each dynamic feature to determine a value for temporal resolution, defined as a frequency at which the temporal modulation transfer falls below a predetermined percentage.

23. The system of claim 21 wherein the at least one processor is further configured to compare the temporal modulation transfer values against frequency to determine a value for temporal resolution, defined as a percentage value at a predetermined frequency.

24. A system for characterizing a temporal resolution of an imaging device, the system comprising:
a phantom composed of at least two materials configured to provide distinct contrast in a reconstructed image formed by the imaging device;
an actuation system configured to move the phantom along a predetermined path to create at least one dynamic feature for imaging by the imaging device.

25. The system of claim 24 wherein the phantom includes at least two materials, one of which is of one density, while another material is of different density and arranged in a pattern to create at least one dynamic feature having a predetermined pattern of features that, when rotated, creates the dynamic feature.

* * * * *

UNITED STATES PATENT AND TRADEMARK OFFICE
CERTIFICATE OF CORRECTION

| | | |
|---|---|---|
| PATENT NO. | : 7,863,897 B2 | |
| APPLICATION NO. | : 12/206279 | |
| DATED | : January 4, 2011 | |
| INVENTOR(S) | : Slocum, Jr. et al. | |

It is certified that error appears in the above-identified patent and that said Letters Patent is hereby corrected as shown below:

Column 1, following the heading STATEMENT REGARDING FEDERALLY SPONSORED RESEARCH, "Not applicable." should be replaced with --This invention was made with Government support under Grant No(s). DAMD17-02-2-0006 awarded by the US Department of the Army. The Government has certain rights in this invention.--

Signed and Sealed this
Thirty-first Day of January, 2012

David J. Kappos
*Director of the United States Patent and Trademark Office*